United States Patent
Nelson et al.

(10) Patent No.: US 11,293,793 B1
(45) Date of Patent: Apr. 5, 2022

(54) BLOOD FLOW MEASUREMENT APPARATUS AND METHOD

(71) Applicant: University of South Alabama, Mobile, AL (US)

(72) Inventors: David Nelson, Spanish Fort, AL (US); Saeed Iftakhar Latif, Mobile, AL (US)

(73) Assignee: University of South Alabama, Mobile, AL (US)

(*) Notice: Subject to any disclaimer, the term of this patent is extended or adjusted under 35 U.S.C. 154(b) by 360 days.

(21) Appl. No.: 16/365,967

(22) Filed: Mar. 27, 2019

Related U.S. Application Data (60) Provisional application No. 62/761,769, filed on Apr. 4, 2018.

(51) Int. Cl.
| | | |
|---|---|---|
| *G01F 1/684* | (2006.01) | |
| *G01F 1/688* | (2006.01) | |
| *A61B 5/01* | (2006.01) | |
| *A61B 5/0205* | (2006.01) | |
| *A61B 5/0265* | (2006.01) | |

(52) U.S. Cl.
CPC ............. *G01F 1/6847* (2013.01); *A61B 5/01* (2013.01); *A61B 5/02055* (2013.01); *G01F 1/688* (2013.01); *A61B 5/0265* (2013.01); *A61B 2562/0271* (2013.01)

(58) Field of Classification Search
CPC ......... G01F 1/6847; G01F 1/688; A61B 5/01; A61B 5/02055; A61B 2562/0271
See application file for complete search history.

(56) References Cited

U.S. PATENT DOCUMENTS

| | | |
|---|---|---|
| 7,267,651 B2 | 9/2007 | Nelson |
| 9,250,139 B2 | 2/2016 | Tofighi |
| 9,320,473 B2 | 4/2016 | Shuler |
| 9,402,573 B2 | 8/2016 | Su |
| 9,610,018 B2 | 4/2017 | Gulati |
| 9,613,911 B2 | 4/2017 | Rogers |
| 9,875,974 B2 | 1/2018 | Rogers |
| 9,877,659 B2 | 1/2018 | Lee |
| 9,888,871 B2 | 2/2018 | Watson |
| 2004/0215086 A1* | 10/2004 | Nelson .................... A61B 5/026 600/504 |
| 2012/0029359 A1* | 2/2012 | Sterzer ..................... A61B 5/01 600/474 |
| 2016/0199131 A1* | 7/2016 | Allison .................. A61B 18/18 606/13 |
| 2017/0224257 A1 | 8/2017 | Rogers |
| 2017/0293735 A1 | 10/2017 | Itu |
| 2018/0014734 A1 | 1/2018 | Rogers |

* cited by examiner

*Primary Examiner* — Daniel L Cerioni
(74) *Attorney, Agent, or Firm* — J. Nevin Shaffer, Jr.

(57) ABSTRACT

An improved skin blood flow measurement apparatus consists of a chassis with an antenna connected with the chassis such that the antenna directs RF energy at an area of a skin surface below the chassis. A temperature sensor is also connected with the chassis such that the temperature sensor is held in fixed relation to the antenna and such that the temperature sensor is also directed to the same said area of a skin surface below the chassis for measurement of temperature of the area and further where the temperature sensor does not contact the skin surface and where the chassis supports the antenna and the temperature sensor in fixed relation to the area.

7 Claims, 4 Drawing Sheets

BLOOD FLOW MEASUREMENT APPARATUS AND METHOD

CROSS REFERENCE TO RELATED APPLICATION

This application claims the benefit of previously filed U.S. provisional patent application No. 62/761,769 filed Apr. 4, 2018 for a "Surface transducer with integrated microstrip antenna and temperature sensor for evaluating skin microcirculation". The Applicant hereby claims the benefit of this provisional application under 35 U.S.C. § 119. The entire content of this provisional application is incorporated herein by this reference.

FIELD OF THE DISCLOSURE

The present invention pertains to an improved blood flow measurement apparatus and method. In particular, according to one embodiment, an improved skin blood flow measurement apparatus consists of a chassis with an antenna connected with the chassis such that the antenna directs RF energy at an area of a skin surface below the chassis. A temperature sensor is also connected with the chassis such that the temperature sensor is held in fixed relation to the antenna and such that the temperature sensor is also directed to the same said area of a skin surface below the chassis for measurement of temperature of the area and further where the temperature sensor does not contact the skin surface and where the chassis supports the antenna and the temperature sensor in fixed relation to the area.

BACKGROUND OF THE INVENTION

Peripheral Artery Disease (PAD) affects 8-12 million people in the US (Khan, Farooqui, and Niazi 2008) and costs the US health care system more than $54 billion annually (Driver et al. 2010). It is associated with systemic atherosclerosis (Pérez-Martin et al. 2010), an increased risk of myocardial infarction and stroke (Jan et al. 2013) and is a strong indicator of future morbidity and mortality (Alandab et al. 2015). Diabetes mellitus is a major risk factor for PAD. Ischemic diabetic foot ulcers (DFU) associated with PAD are a common cause of morbidity among adult diabetics (Ikem et al. 2010).

While intermittent claudication is the classic symptom, most patients with PAD are asymptomatic or have atypical symptoms (Winfrey et al. 2011). Screening is limited and most are not diagnosed until they present with complications (claudication, skin ulcers) (Mohler et al. 2004). This often necessitates aggressive treatment, with higher costs and poorer outcomes than could be obtained with earlier interventions.

New recommendations from the American Heart Association (AHA) and American College of Cardiology (ACC) include screening everyone greater than or equal to 65 years old and all patients with two or more risk factors for PAD. Risk factors include obesity, age greater than 50 years, diabetes, and a history of smoking (Gerhard-Herman et al. 2016). Implementing the new AHA/ACC guidelines will entail screening tens of millions of Americans. This presents a prospectively enormous resource challenge and cost to primary care providers and clinics.

Thus, there is an urgent need for a simple, fast and easy point-of-care technology for rapid assessment of skin blood flow in the periphery which can provide an initial screening tool to identify patients for follow-up evaluation (such as Ankle-Brachial Index measurement).

The current primary PAD diagnostic tool is measurement of the Ankle-Brachial Index (ABI), which is the ratio of systolic pressure in the dorsalis pedis or posterior tibial arteries to the higher of the left and right brachial artery systolic pressures, as measured on a supine subject. ABI measurement is slow, cumbersome, requires specialized training and is not generally reimbursable (Kuller 2001; Mohler et al. 2004; Pearson, Kukulka, and Ur 2009; Sheikh et al.). Millimeter Wave (MMW) Flow Sensing offers a potential method for quick and easy assessment of flow in the peripheral vasculature. "Millimeter Wave" refers to that part of the radio frequency spectrum in the range 30-300 GHz. Energy in the MMW band is characterized by shallow penetration in tissue (typically <1 mm, depending on frequency). This method (MMW flow sensing) could facilitate expanded primary care screening for PAD.

Current embodiments of the radio frequency (RF)/MMW flow sensing technology require bulky, expensive hardware that is not suitable for point-of-care use. That is, the current state of the art transmitter and sensor system for RF/MMW assessment of skin blood flow relies on a bulky and expensive horn antenna to irradiate the skin surface while monitoring the skin surface temperature with a separate infrared (IR) camera or similar device. That system requires careful independent positioning and alignment of both the horn antenna and IR camera with respect to the skin surface to achieve consistent heating and temperature measurements. As a result the procedure is slow and has poor repeatability due to inconsistent heating due to positioning errors among other reasons.

There is a need for a compact, rugged and easy-to-use feasible RF antenna and sensor system for assessment of flow in the peripheral skin microvasculature.

Furthermore, there is a need for a feasible RF transmitter and sensor system to achieve controlled RF heating of the skin with simultaneous surface temperature measurement.

There is a need for a non-invasive device which offers easier and consistent positioning relative to the skin surface.

There is a need for a non-invasive device which offers a very substantial cost savings over prior devices.

SUMMARY

Accordingly, a preferred embodiment of the present invention consists an improved skin blood flow measurement apparatus with a chassis with an antenna connected with the chassis such that the antenna directs radio frequency (RF) energy at an area of a skin surface below the chassis. A temperature sensor is also connected with the chassis such that the temperature sensor is held in fixed relation to the antenna and such that the temperature sensor is also directed to the same said area of a skin surface below the chassis for measurement of temperature of the area and further where the temperature sensor does not contact the skin surface and where the chassis supports the antenna and the temperature sensor in fixed relation to the area.

All terms used herein are given their common meaning to those of ordinary skill in the art.

In one aspect, the chassis further consists of a chassis body where the antenna and the temperature sensor are connected with the chassis body in fixed relation to each other such that the antenna and the temperature sensor both are directed at the same area of the skin surface; and a surface support connected with the chassis body where the surface support contacts the skin surface and supports the chassis body above the skin surface.

In a further aspect, the chassis body further comprises an inverted "V" body with a pair of downward facing legs connected at one end and spread apart to form two surface supports where the antenna is connected with one leg and where the temperature sensor is connected with the other leg and where the antenna and the temperature sensor are directed to the same area of skin surface below the inverted "V".

In another aspect, the antenna consists of a micro-strip antenna transmitting RF energy.

In one aspect, the micro-strip antenna is designed to operate in the frequency range of 26.5 GHz to 40 GHz.

In a further aspect, an amplifier is operably connected to the micro-strip antenna and a RF signal generator is operably connected to the amplifier.

In one aspect, the invention further includes a controller where the controller is connected with the micro-strip antenna for controlling RF ranges and where the controller is connected with the temperature sensor for operation of the temperature sensor and for obtaining temperature data from the temperature sensor. In another aspect, the invention further includes a processor connected with the controller for receipt and recording and analysis of the temperature data and micro-strip antenna range data.

In another aspect, the temperature sensor is an infrared temperature sensor.

According to another embodiment, a skin blood flow measurement apparatus consists of a chassis with a chassis body and a surface support is connected with the chassis body where the surface support contacts a skin surface and supports the chassis body above the skin surface. An antenna is connected with the chassis body such that the antenna directs RF energy at an area of the skin surface below the chassis and where the antenna consists of a micro-strip antenna. A temperature sensor is also connected with the chassis body such that the temperature sensor is held in fixed relation to the antenna and such that the temperature sensor is also directed to the same area of a skin surface below the chassis for measurement of temperature of the area and where the temperature sensor does not contact the skin surface and where the chassis body supports the antenna and the temperature sensor in fixed relation above the area.

In one aspect, the chassis further comprises a surface support connected with the chassis body where the surface support contacts the skin surface and supports the chassis body above the skin surface. In one particular aspect, the chassis body further consists of an inverted "V" body with a pair of downward facing legs connected at one end and spread apart to form two surface supports where the antenna is connected with one leg and where the temperature sensor is connected with the other leg and where the antenna and the temperature sensor are directed to the same area of skin surface below the inverted "V".

In another aspect, the micro-strip antenna is designed to operate in the frequency range of 26.5 GHz to 40 GHz.

In a further aspect of this embodiment, an amplifier is operably connected to the micro-strip antenna and a RF signal generator is operably connected to the amplifier.

In one aspect, the invention further includes a controller where the controller is connected with the micro-strip antenna for controlling RF ranges and where the controller is connected with the temperature sensor for operation of the temperature sensor and for obtaining temperature data from the temperature sensor. In another aspect, the invention further includes a processor connected with the controller for receipt and recording and analysis of the temperature data and micro-strip antenna range data.

In another aspect, the temperature sensor is an infrared temperature sensor.

According to another embodiment, a method of calculating a blood flow rate in an area of the skin using the temperature sensor and antenna system described above includes the steps of:

a. generating an electrical signal having a power output;
b. irradiating the area of skin surface with the electrical signal;
c. determining an incident power density of the electrical signal as a function of the power output and dimensions of the area being irradiated;
d. heating the area in response to irradiating the area;
e. sensing the temperature of the area within a time period; calculating the temperature change of the area; and
f. calculating the blood flow rate in the area based on the power density of the electrical signal and the temperature change and/or the rate of temperature change of the area; wherein the electrical signal includes a frequency in the RF band.

In another aspect of the method, the chassis further consists of a surface support connected with the chassis body where the surface support contacts the skin surface and supports the chassis body above the skin surface.

In a further aspect of the method, the micro-strip antenna is designed to operate in the frequency range of 26.5 GHz to 40 GHz.

Further, one embodiment of the present invention is a non-invasive device for measuring or assessing skin microcirculatory blood flow in the periphery (of a subject) comprising a surface transducer system integrating at least one microstrip antenna transmitting RF energy and at least one non-contacting temperature sensor for simultaneous surface temperature measurement.

Another embodiment of the present invention includes a temperature sensor and antenna system comprising: (i) a non-invasive device for measuring or assessing skin microcirculatory blood flow in the periphery comprising a surface transducer system integrating at least one micro-strip antenna transmitting RF energy and at least one non-contacting temperature sensor for simultaneous surface temperature measurement; (ii) an amplifier operably connected to the surface transducer system; and (iii) an RF signal generator operably connected to the amplifier. The temperature sensor and antenna system can further comprise a processor, output device and/or server (all operably connected thereto).

DESCRIPTION OF THE DRAWINGS

Other objects, features and advantages of the present invention will become more fully apparent from the following detailed description of the preferred embodiment, the appended claims and the accompanying drawings in which:

DETAILED DESCRIPTION OF EMBODIMENTS

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the invention be regarded as including equivalent constructions to those described herein insofar as they do not depart from the spirit and scope of the present invention.

For example, the specific sequence of the described process may be altered so that certain processes are conducted in parallel or independent, with other processes, to the extent that the processes are not dependent upon each other. Thus, the specific order of steps described herein is not to be considered implying a specific sequence of steps to perform the process. In alternative embodiments, one or more process steps may be implemented by a user assisted process and/or manually. Other alterations or modifications of the above processes are also contemplated. For example, further insubstantial approximations of the process and/or algorithms are also considered within the scope of the processes described herein.

In addition, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

It should also be noted that a plurality of hardware and software based devices, as well as a plurality of different structural components, may be utilized to implement the invention. Furthermore, and as described in subsequent paragraphs, the specific configurations illustrated in the drawings are intended to exemplify embodiments of the invention and that other alternative configurations are possible.

The present invention includes an improved, non-invasive, blood flow measuring device, including in pertinent part, a temperature and antenna system, and a method of calculating blood flow based on the system. An essential feature of the present invention is a non-invasive blood flow measurement device provided by the novel integration of one or more microstrip antenna and one or more non-contacting temperature sensor(s) attached to a chassis so as to create a surface transducer system capable of accurate and controlled RF heating of the skin with simultaneous surface temperature measurement.

The resulting non-invasive device is compact and rugged while providing improved assessment of skin blood flow in the skin microvasculature. This non-invasive device offers easier and more consistent positioning relative to the skin surface.

With respect to the device, the present invention is a non-invasive device for measuring or assessing skin microcirculatory blood flow comprising a surface transducer system integrating at least one microstrip antenna transmitting RF energy and at least one non-contacting temperature sensor on a chassis for simultaneous surface temperature measurement.

Surface transducer is defined as a transducer placed on or near the skin's surface. As used herein the "surface transducer" is found in the temperature sensor which records surface temperature and converts it to an electrical voltage signal transmission which is then correlated to a blood flow measurement. That is, the temperature sensor of the present invention converts a physical variable, temperature, into an electrical signal which is directly correlated to blood flow as more fully described herein. Further, the type of microstrip antenna suitable for use in the present invention is a custom made component designed for a specific frequency. Still further, suitable temperature sensors include, but are not limited to, Melexis 90614 and Texas Instrument TMP007 brand temperature sensors or any temperature sensor now known or hereafter developed that satisfy the requirements of the present invention as set forth herein. Together, the temperature sensor and antenna and chassis combination creates the "surface transducer system" according to the requirements of the present invention.

By way of description, with respect to the system, the present invention is a temperature sensor and antenna system consisting preferably of: (i) a non-invasive device for measuring or assessing skin microcirculatory blood flow comprising an antenna integrating at least one micro-strip antenna transmitting RF energy and at least one non-contacting temperature sensor for simultaneous surface temperature measurement; (ii) an amplifier operably connected to the antenna; and (iii) an RF signal generator operably connected to the amplifier. The transmitter and antenna system preferably further includes a processor, output device and/or server (all operably connected thereto).

Suitable amplifiers include, but are not limited to, Ducommun AHP-35012520-02 brand amplifiers.

Suitable RF signal generators include, but are not limited to, Ducommun OGL-28350110-01 brand amplifiers.

Suitable processors include any computer or other device operable to receive data, manipulate data, perform calculations, display information, and/or perform similar functions as are now known or hereafter developed.

Suitable servers include any device operable to store information related to blood flow data. The server can include any operating system for running various software programs and/or a communications application.

Suitable output devices include, but are not limited to, LED devices and LCD device.

With respect to the method, the present invention consists of a method of calculating or determining a blood flow rate (or a metric based on or reflective of blood flow rate of perfusion) in an area using the temperature sensor and antenna system of the present invention, the method consisting of: (i) generating an electrical signal having a power output; (ii) irradiating the area with the electrical signal; (iii) determining an incident power density of the electrical signal as a function of the power output and dimensions of the area being irradiated; (iv) heating the area in response to irradiating the area; (v) sensing the temperature of the area within a time period; calculating the temperature change and/or the rate of temperature change of the area; and (vi) calculating the blood flow rate in the area based on the power density of the electrical signal and the rate of temperature change of the area; where the electrical signal includes a frequency in the millimeter wave band.

It should be noted that the present invention can include a method similar in nature to the aforesaid method, but where the blood flow rate can also be determined based on calibration data. For example, one could have a look-up table of temperature increases versus flow rate at a given power. Further, it should be understood that various safety features are included within the scope of the invention such as controls to prevent overheating and the like.

Operations

Figure 5:
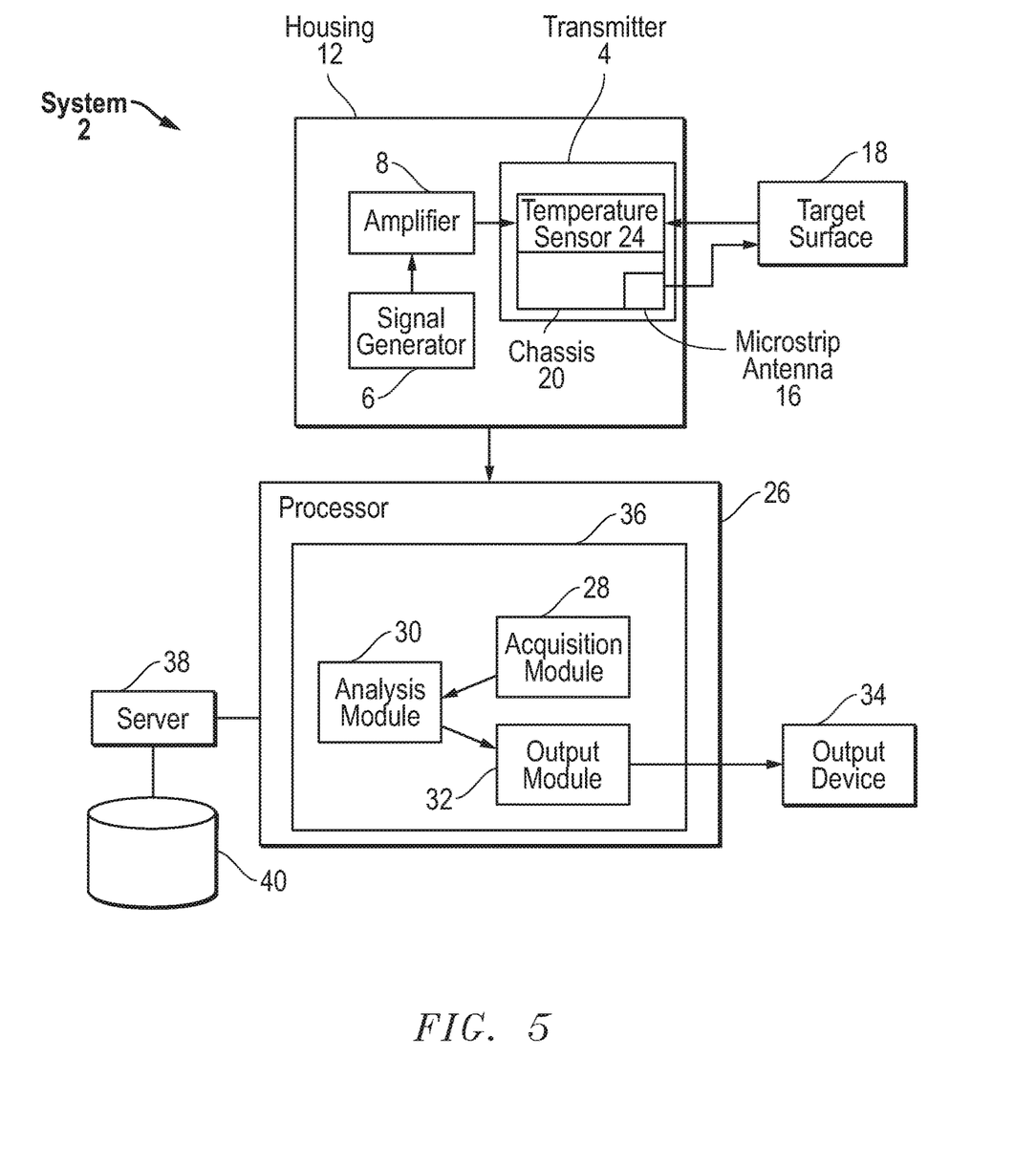
FIG. 5 is a block diagram of a feasible transmitter and antenna system for measuring blood flow.

In one embodiment of the present invention, a system 2 is disclosed as shown in FIG. 5. The preferred system 2 includes a transmitter/antenna 4, (which preferably includes a RF signal generator 6 and a RF amplifier 8) as part of a surface transducer system 10. The transmitter/antenna 4 is preferably supported in (and protected by) a housing 12. The signal generator 6 generates an electrical signal preferably having a frequency in the range of 26 kHz to about 40 GHz. More specifically, the signal generator 6 generates an electrical signal preferably having a frequency of 35 GHz.

Generally, the electrical signal is low power. As used herein, the term "low power" means a power output that provides an incident power density of less than 1 W/cm squared of the projected surface area normal to the direction of propagation.

Figure 6:
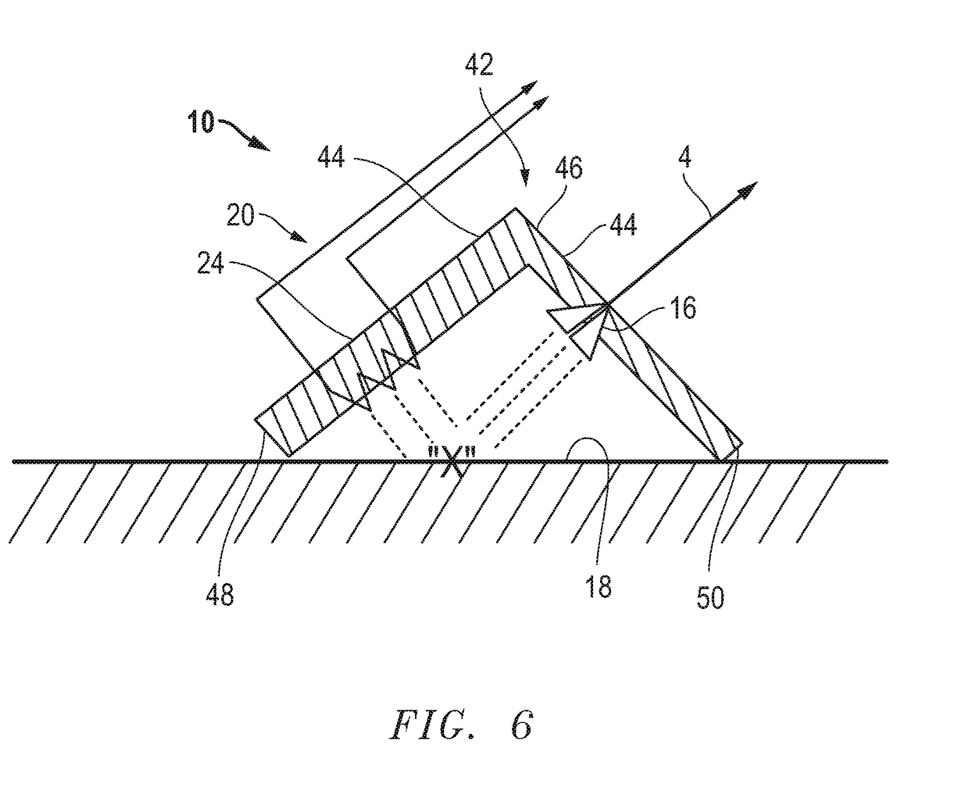
FIG. 6 is a side view of the inverted "V" chassis according to one embodiment.

The transmitter/antenna 4 preferably consists of a microstrip antenna 16 which can be housed within and/or fixed upon a chassis 20 along with an infrared temperature sensor 24 (See FIG. 6 for example). Together, the transmitter/antenna 4, the temperature sensor 24 and the chassis 20 make up the surface transducer system 10 of the present invention. The microstrip antenna 16 is operably integrated into the surface transducer system 10 which is operably integrated into the transmitter/antenna 4 to receive and provide the electrical signal to a target surface 18 (i.e., the portion of the tissue that is exposed to the signal) on the subject (not shown). The target surface 18 can include multiple layers and thicknesses and is not limited to the top or surface that contacts the electrical signal. The microstrip antenna 16 is operably contained within the transmitter/antenna 4 to receive the electrical signal.

The electrical signal irradiates the target surface 18 at a particular location "X" as shown in FIG. 6. The electrical signal has an associated power density value when applied to the target surface 18. The power density is a function of the electrical signal power and the dimensions of the target area, and is contemplated to be generally less than about 1 W/cm squared when used to irradiate the skin tissue of a human subject (not shown). The incident power density of the electrical signal on the target surface 18 is a function of the electrical signal power, the dimensions of the target surface 18, and the angle of incidence of the electrical signal with respect to the target surface 18. The angle of incidence of the electrical signal can affect the amount of energy from the electrical signal that the target surface 18 can absorb. The target surface 18 has an associated absorption coefficient, which is a fraction of the incident energy that is absorbed by the medium of the target surface 18. The absorption coefficient can vary with the frequency of the electrical signal. Generally, the target surface 18 is planar and the angle of incidence of the electrical signal is equal to or less than 90 degrees. The absorption coefficient of a non-planar surface can also be determined. All of this highlights the importance of the chassis 20 of the present invention which fixes the location of the surface transducer system 10, the antenna 4 and the temperature sensor 24 with relation to each other on the chassis 20 and to the area "X" of the skin below the chassis 20 to which they are directed, both of which have heretofore been independent.

Transmitter/antenna 4 is intended to operate at a fixed power density, which means that the power output of the electrical signal is fixed, and the targeted surface 18 is expected to be maintained at a preselected and fixed distance from the transmitter/antenna 4. If the transmitter/antenna 4 is not intended to operate at a fixed power density, the system 2 may include a means for calibrating the transmitter/antenna 4 to accommodate changes in the environment surrounding the transmitter/antenna 4 or changes in the parameters of the blood flow rate measurement procedure. For example, the transmitter/antenna 4 may include a means for calibration that permits the power and/or frequency of the electrical signal to be adjusted. Further, in the case where more than one transmitter/antenna 4 is used, multiple power and/or frequencies may be used as well according to the principles of the invention.

The system 2 preferably includes an infrared temperature sensor 24 capable of being integrated (along with the microstrip antenna 16) into a chassis 20 to make up the surface transducer system 10. The infrared temperature sensor 24 is designed to sense a temperature of the target surface 18. The infrared temperature sensor 24 integrated within the surface transducer system 10 (which includes the transmitter/antenna 4) on chassis 20 and is positioned adjacent to the target surface 18 to sense/detect a temperature change as a result of the application of the electrical signal generated on the target surface 18 at location "X" by the signal generator 6 through transmitter/antenna 4. As used herein with respect to the infrared temperature sensor 24, the term "adjacent" means positioned close enough to the target surface 18 to accurately sense a temperature of the target surface 18 whether or not the temperature sensor 24 actually touches the target surface 18, which it preferably does not.

The frequency and the properties of the target surface 18 affect the penetration depth of the electrical signal in the target surface 18. Penetration depth is the depth at which power density has decreased to 13.5% of the power density at the surface. Generally, the penetration depth of human skin is in the range of about 0.1 mm to about 1.0 mm for frequencies in the range of about 300 GHz to about 30 GHz, respectively. The result of the combination of elements as set forth herein is that the system 2 thereby measures the rate of blood flow in the target surface 18.

The system 2 preferably includes a processor 26, which is electrically connected to the temperature sensor 24. The processor 26 preferably includes circuitry (not shown), such as a signal conditioning circuit, to receive and/or process the signal(s) from the infrared temperature sensor 24. The processor 26 can be electrically connected to the transmitter/antenna 4 and/or the data, such as the characteristics of the electrical signal, from the transmitter/antenna 4 can be manually entered into the processor 26. The processor 26 can be a computer or any other device operable to receive data, manipulate data, perform calculations, display information, and/or perform similar functions. The processor 26 can include I/O interfaces and storage devices or memory (not shown). The processor 26 communicates and receives commands from input devices such as a keyboard and a mouse (not shown).

The processor 26 preferably includes a software program 36. The software program 36 includes an acquisition module 28, an analysis module 30, and an output module 32. As noted above, the function and operation of the software program 36 can be encompassed in suitable hardware components and/or modules. The acquisition module 28 is operable to acquire and receive data manually entered into the processor 26 and data from the infrared temperature sensor 24 and the transmitter/antenna 4. The analysis module 30 is electrically connected to the acquisition module 28. The analysis module 30 is operable to receive the data from the acquisition module 28 and analyze the data. The analysis module 30 can perform any mathematical function, manipulate the data, correlate the data, format the data, and/or perform any other analysis technique. The output module 32 can be electrically connected to the acquisition module 28 and/or the analysis module 30. The output module 32 is operable to receive data from the acquisition module 28, receive data from the analysis module 30, format the data, and output the data to a monitor, a display, and/or a printer, (collectively referred to as an output device 34).

The system 2 can include a server 38 and/or a database 40 for storing information related to blood flow data. The server 38 can include an operating system for running various software programs (not shown) and/or a communications application (not shown). The software programs can be manipulated by computer terminals (not shown) and/or medical equipment (not shown) to acquire, enter, review, and/or save information. The processor 26 can interface with and/or connect to the server to upload information and/or download information. In addition, the software program 36 can reside on the server 38.

The following is an illustrative example of one method of the present invention relating to blood flow rate calculation. In preparation for determining a blood flow rate of a target surface 18, the system 2 activates the software program 36 and the transmitter/antenna 4. In addition, the infrared temperature sensor 24 is positioned adjacent to the target surface 18 by means of the chassis 20 of the present invention. The processor 26 communicates with the temperature sensor 24 to measure an initial temperature of the target surface 18. The initial temperature can be determined by taking a plurality of measurements over a period of time. The transmitter/antenna 4 can generate an electrical signal having a frequency in the range of 26 kHz to about 40 GHz. preferably a frequency of 35 GHz.

From its fixed location on the chassis 20, an electrical signal is directed by the transmitter/antenna 4, preferably by means of the microstrip antenna 16, toward the target surface 18 at the same area "X" to which the temperature sensor 24 is directed. The electrical signal can be modified by entering the operably integrated printed microstrip antenna section 16 of the surface transducer 10 to accommodate the desired size of the target surface 18. The temperature of the target surface 18 changes temperature as a result of the application of the electrical signal to the target surface 18, i.e., heats. The temperature sensor 24 detects the changes in temperature of the target surface 18 over a period of time. As an example, the temperature sensor 24 can detect a change in temperature of the target surface 18 every second or any other time interval. The time period over which the electrical signal is applied and during which the temperature sensor 24 detects temperature changes of the target area is typically less than one minute (for humans). However, the electrical signal can be applied to the target surface 18 for more than one minute and the temperature sensor 24 can detect temperature changes of the target surface 18 beyond the one minute time period.

The acquisition module 28 of the processor 26 receives the temperature data from the temperature sensor 24. The analysis module 30 analyzes the temperature data to determine the change in temperature of the target surface 18 over the period of time that the electrical signal was applied to the target surface 18. The analysis module 30 can also receive a power density value and an absorption coefficient that is either manually entered into the processor 26 and/or received from the transmitter/antenna 4. For example, the user may enter into the processor 26 a value for the size of the target surface 18 in square centimeters, or the processor 26 may receive a fixed power density value from the transmitter/antenna 4.

The analysis module 30 calculates a blood flow rate in the target surface 18 based on the rate of temperature change, for example only and not by way of limitation, and the power density value. The output module 32 can receive the blood flow rate and corresponding formatting data and transfer to the output device 34. The output device 34 can display and/or print the data. The data can be formatted to include raw data, measurements, unanalyzed data, analyzed data, images, charts, graphs, identified abnormalities, normal and abnormal ranges, patient identifiers (such as name, age, sex, weight, race), patient history (for instance, cholesterol level, diabetes, family history, smoking, blood pressure, obesity), symptoms, dates of reports and tests, and identification of prescribing, attending and reading physicians. The blood flow rate data can be used to provide a health assessment of the subject.

Test

The feasibility of using a microstrip patch antenna, operating at a frequency of 35 GHz in a Millimeter Wave flow transducer was tested as set forth below.

Millimeter Wave (MMW) flow sensing uses a radio frequency (RF) energy source to produce a mild heating of the skin. The temperature of the skin can be related to the blood flow in the underlying microvasculature through application of Fick's Principle. This relationship has been demonstrated in vivo in both humans and in animal models (Walters et al. 2004; Nelson et al. 2003) subjected to low-power (<30 dBm) MMW radiation in the W band (75-110 GHz) under far-field exposure conditions.

As the depth of energy penetration is a function of wavelength, it is possible to heat the tissue to the depth of the papillary plexus (approx. 0.5 mm) by specifying an appropriate MMW frequency (such as, for example only and not by limitation, Ka band, 26.5-40 GHz). This can produce a surface temperature response that is sensitive to blood flow in the plexus and microcirculation of the papillary dermis.

Figure 1:
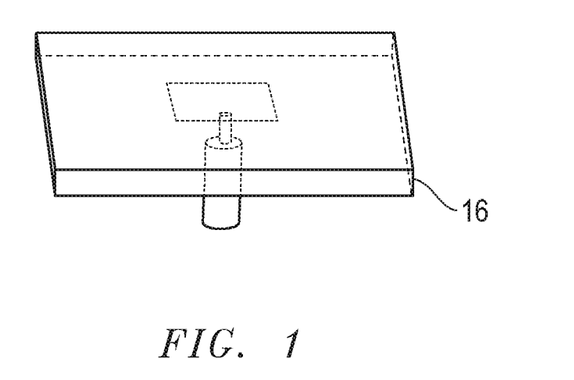
FIG. 1 is an illustration of a microstrip antenna designed for an operating frequency of 35 GHz.

The present invention, preferably, utilizes a small microstrip patch antenna 16 as the radiating surface. The antenna, which is designed to operate at a frequency of 35 GHz (Ka band), consisted of a rectangular copper patch (2.6 mm×2.9 mm) on a 12 mm×12 mm dielectric substrate (Rogers RT/Duroid® 5880) as shown in FIG. 1.

Figure 2:
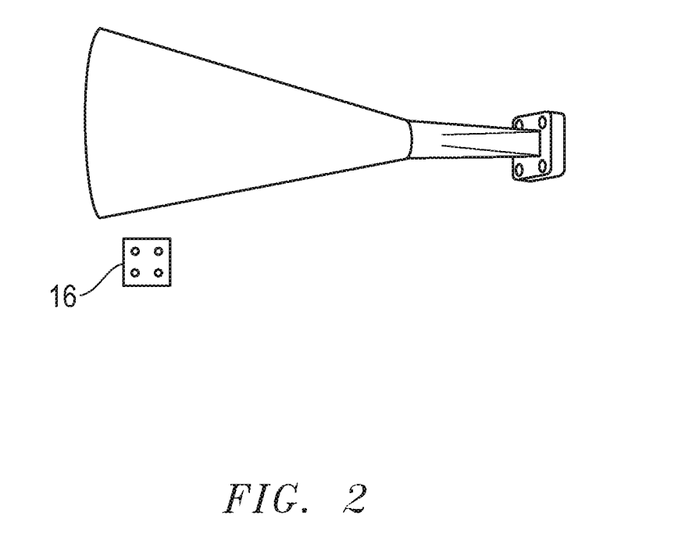
FIG. 2 is a photograph of a Ka band horn antenna (top) is shown next to a microstrip antenna (bottom). The microstrip is the small copper rectangle on the larger black substrate.

The microstrip antenna 16 offers substantial size reduction, compared with a horn antenna as shown in FIG. 2 and can be incorporated into a surface transducer system 10 much more readily than can a horn antenna. This provides for easier and more consistent positioning relative to the skin surface. Further, because the microstrip patch can be printed on the substrate, it offers a very substantial cost savings over a horn antenna.

In order to solve the problems associated with prior art devices and methods, it is understood that the improved apparatus and method must include a temperature sensor and antenna system 2 capable of repeatably heating the skin sufficient to resolve flow rate, within a time window sufficiently short to avoid a vasoactive response. The microstrip antenna 16 according to the present invention was evaluated in vitro to determine the ability to consistently heat a phantom skin material (SynDaver Labs, Tampa, Fla.) under near-field exposure conditions. The antenna was driven at 35 GHz (nom.) with a transmitter consisting of a Gunn oscillator and an RF power amplifier. The phantom material was heated for 60 sec with the antenna oriented normal to the phantom surface at distances of 2-4 mm, corresponding to one-quarter to one-half of the wavelength in free space (8.5 mm). Temperature of the phantom material was measured with an infrared camera (Flir T420, Flir Systems Inc., Wilsonville, Oreg.).

The ability to detect changes in perfusion was tested by scoring a series of flow channels in the underside of the phantom. The material was perfused with deionized water in a custom-built flow chamber using a syringe pump (PHD 2000, Harvard Apparatus, Holliston, Mass.) to control and adjust the flow rate. A heat exchanger on the inlet side controlled water temperature. Temperature response to MMW heating was measured with a single infrared sensor (MLX 90614, Melexis NV, Ypres, Belgium).

Results

Figure 3:
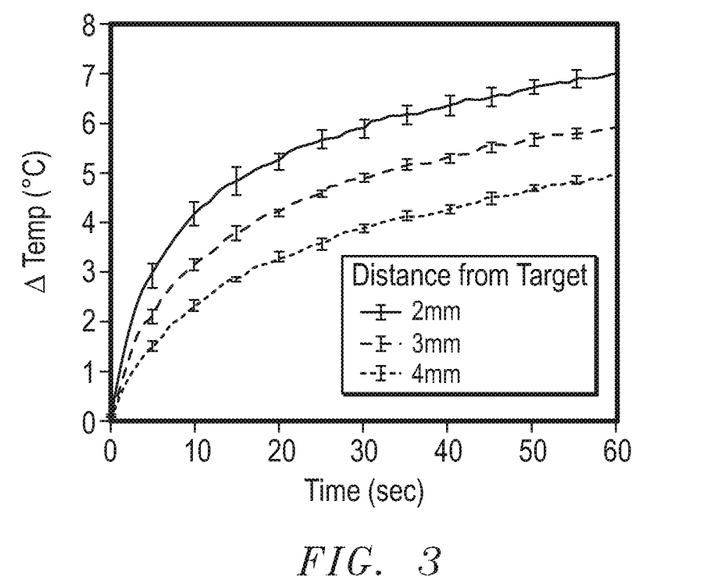
FIG. 3 is an ensemble heating curve for a microstrip antenna driven at frequency of 35 GHz. Error bars represent ±1 s.d.

Heating curves for the unperfused phantom are shown for three different antenna spacings (2, 3 and 4 mm) as FIG. 3. The ensemble (N=5) temperature increases are shown with standard deviations for each 5th data point.

The temperature sensor and antenna system 2 produced the greatest surface temperature increase at the closest separation between antenna and skin (d=2 mm). The magnitude of the temperature decreases as the antenna spacing is increased.

Figure 4:
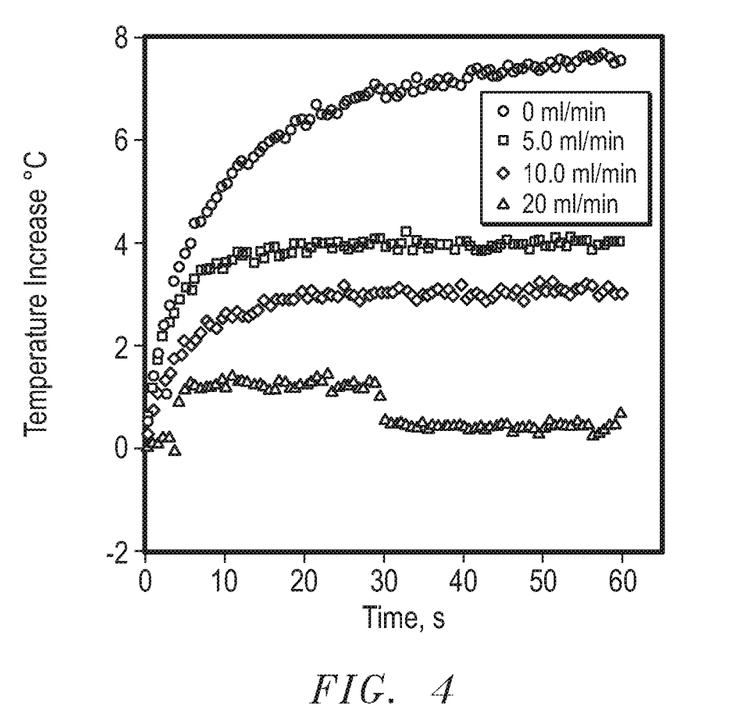
FIG. 4 is a graphical representation of the temperature increase of phantom during 60 minutes of heating for four different flowrates.

The results of a single series of perfusion experiments are shown as FIG. 4. The antenna spacing (centerline distance from target) was 2 mm. Temperature of the irradiated region was measured at six flow rates: 0, 2.5, 5.0, 7.5, 10.0 and 20.0 ml/min. The 2.5 and 7.5 ml/min results are not shown in FIG. 4 so as to preserve clarity of the graph. They followed the trend shown by the other flow conditions (FIG. 4), in that higher flow rates resulted in smaller temperature increases.

Interpretation

The microstrip antenna and temperature sensor fixed on a chassis in combination produced repeatable temperature increases in a synthetic phantom material under near-field exposure conditions. Standard deviation of the temperature is highest at the closest separation distance (d=2 mm). This may be associated with sensitivity to slight variations in the antenna positioning relative to the target phantom.

For flow measurements to be feasible, the antenna must be capable of reproducible heating the skin at close range, while allowing sufficient separation to allow measurement of the surface temperature with an IR sensor or camera. The magnitude of the surface temperature must be sufficient to allow sufficient resolution of flow rates without burning the skin.

The microstrip antenna 16 demonstrates sufficient heating and repeatability for incorporation in a flow measurement transducer. The rate of heating, at an antenna spacing of 2 mm proved capable of resolving flow rates within the physiological range.

Referring now to FIG. 6 chassis body 20 in one embodiment is an inverted "V" body 42 structure with a pair of downward facing legs 44 connected at one end 46 and spread apart to form two surface supports 48 and 50 where microstrip antenna 16 is connected with one leg 44 and where temperature sensor 24 is connected with the other leg 44 in fixed relation to each other and where the microstrip antenna 16 and the temperature sensor 24 are directed to the same area "X" of skin surface 18 below the inverted "V" body 42.

The description of the present embodiments of the invention has been presented for purposes of illustration, but is not intended to be exhaustive or to limit the invention to the form disclosed. Many modifications and variations will be apparent to those of ordinary skill in the art. As such, while the present invention has been disclosed in connection with an embodiment thereof, it should be understood that other embodiments may fall within the spirit and scope of the invention as defined by the following claims.

What is claimed is:

1. A skin blood flow measurement apparatus comprising:
   a. a chassis;
   b. an antenna connected with said chassis such that said antenna directs RF energy at an area of a skin surface below said chassis wherein said antenna is configured to not contact said skin surface;
   c. a temperature sensor also connected with said chassis such that said temperature sensor is held in fixed relation to said antenna and such that said temperature sensor is also directed to the same said area of a skin surface below said chassis for measurement of temperature of said area and wherein said temperature sensor is configured to not contact said skin surface and wherein said chassis supports said antenna and said temperature sensor in fixed relation to said area;
   d. a chassis body, wherein said antenna and said temperature sensor are connected with said chassis body in fixed relation to each other such that said antenna and said temperature sensor both are directed at the same area of said skin surface; and
   e. a surface support connected with said chassis body wherein said surface support contacts said skin surface and supports said chassis body above said skin surface wherein said chassis body further comprises an inverted "V" body with a pair of downward facing legs connected at one end and spread apart to form two surface supports wherein said antenna is connected with one leg and wherein said temperature sensor is connected with the other leg and wherein said antenna and said temperature sensor are directed to the same area of skin surface below said inverted "V".

2. The apparatus of claim 1 wherein said antenna comprises a micro-strip antenna transmitting RF energy.

3. The apparatus of claim 2 wherein said micro-strip antenna is designed to operate in the frequency range of 26.5 GHz to 40 GHz.

4. The apparatus of claim 2 further including:
   a. an amplifier operably connected to said micro-strip antenna; and
   b. a RF signal generator operably connected to said amplifier.

5. The apparatus of claim 4 further including a controller wherein said controller is connected with said micro-strip antenna for controlling RF ranges and wherein said controller is connected with said temperature sensor for operation of said temperature sensor and for obtaining temperature data from said temperature sensor.

6. The apparatus of claim 5 further including a processor connected with said controller for receipt and recording and analysis of said temperature data and micro-strip antenna range data.

7. The apparatus of claim 1 wherein the temperature sensor is an infrared temperature sensor.

\* \* \* \* \*